United States Patent
Berg et al.

(10) Patent No.: US 10,412,910 B2
(45) Date of Patent: Sep. 17, 2019

(54) **SMALL SEEDED CORN SALAD (*VALERIANELLA LOCUSTA*)**

(71) Applicant: RIJK ZWAAN ZAADTEELT EN ZAADHANDEL B.V., De Lier (NL)

(72) Inventors: Jurjen Johannes Berg, De Lier (NL); Grit Anja Glawe, De Lier (NL)

(73) Assignee: RIJK ZWAAN ZAADTEELT EN ZAADHANDEL B.V., De Lier (NL)

(*) Notice: Subject to any disclaimer, the term of this patent is extended or adjusted under 35 U.S.C. 154(b) by 324 days.

(21) Appl. No.: 14/592,443

(22) Filed: Jan. 8, 2015

(65) Prior Publication Data

US 2015/0125588 A1    May 7, 2015

Related U.S. Application Data

(63) Continuation-in-part of application No. PCT/EP2013/064843, filed on Jul. 12, 2013.

(30) Foreign Application Priority Data

Jul. 13, 2012 (EP) .................. 12176439

(51) Int. Cl.
    *A01H 5/10* (2018.01)
    *A01H 5/08* (2018.01)
    *A01H 1/04* (2006.01)
    *A01H 5/12* (2018.01)
    *A23L 19/00* (2016.01)

(52) U.S. Cl.
    CPC .............. *A01H 5/08* (2013.01); *A01H 1/04* (2013.01); *A01H 5/10* (2013.01); *A01H 5/12* (2013.01); *A23L 19/00* (2016.08)

(58) Field of Classification Search
    CPC ....................................... A01H 5/10
    See application file for complete search history.

(56) References Cited

PUBLICATIONS

Jacobs et al 2010, International Journal of Plant Sciences 171(4): 421-434.*
Znidarcic et al 2008 Acta Agriculturae Slovenica 91: 59-66.*
Muminovic et al 2003, Proceedings of the EUCARPIA Meeting on Leafy Vegetables Genetics and Breeding, Noordwijkerhout, The Netherlands, Mar. 19-21, 2003, Centre for Genetic Resources Publisher.*
J. Muminovic, et al., Genetic Diversity in Cornsalad (*Valerianella locusta*) and Related Species as Determined by AFLP Markers, Plant Breeding (2004) vol. 123, p. 460-466.

* cited by examiner

*Primary Examiner* — David H Kruse
(74) *Attorney, Agent, or Firm* — Duane Morris LLP; Thomas J. Kowalski; Deborah L. Lu

(57) ABSTRACT

The invention relates to a corn salad fruit of the species *Valerianella locusta*, characterized by a fruit width which is smaller than 1.7 mm and/or a length/width ratio of the fruits which is higher than 1.2, and which fruit width and/or length/width ratio are/is determined by a genetic determinant which is as found in, or is obtainable from, fruits of which a representative sample was deposited under accession number NCIMB 42007, or is equivalent to the said genetic determinant in NCIMB 42007.

9 Claims, 2 Drawing Sheets

A)

B)

C)

D)

SMALL SEEDED CORN SALAD (*VALERIANELLA LOCUSTA*)

RELATED APPLICATIONS AND INCORPORATION BY REFERENCE

This application is a continuation-in-part application of international patent application Serial No. PCT/EP2013/064843 filed Jul. 12, 2013, which published as PCT Publication No. WO 2014/009555 on Jan. 16, 2014, which claims benefit of European patent application Serial No. 12176439.3 filed Jul. 12, 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to small uniform sized fruits of corn salad, to plants grown from the fruits, progeny from the fruits and plants and to a method for producing such a plant.

*Valerianella locusta* or corn salad is a small weedy looking vegetable that grows in a basal rosette of round to spoon shaped leaves up to 15 cm long. The leaves are tender, smooth and slightly succulent. Corn salad, also known as lamb's lettuce, is a member of the family Valerianacea. It is an annual winter plant which is a common weed in waste ground and cultivated land but has also been cultivated for a long time. It is mainly grown in continental Europe where it is a favorite salad plant in France and Germany.

During the last decades, corn salad has become an increasingly important economic crop. Up to 75% of the world production is produced in France. The production area in Germany in open field is 1700 ha and in greenhouses the production area is 200 ha. Based on area corn salad is herewith the third most important greenhouse grown vegetable crop in Germany, after tomato and cucumber. Corn salad is achieving more importance and consequently attracts an increasing interest of plant breeders.

Corn salad breeding has resulted in cultivated corn salad varieties that share favorable morphological characteristics, have acquired relevant disease resistances, and are often adapted to a certain growing season or specifically developed for year-round cultivation. The shape, color, thickness, and size of the leaves, as well as compactness and vigor of the plants, are important traits that are considered in breeding for corn salad varieties.

Cultivated corn salad of the species *Valerianella locusta* can be easily distinguished phenotypically from wild populations of *V. locusta*, and the plant habit is clearly different from plant populations of other *Valerianella* species such as *V. carinata* or *V. rimosa* (FIG. 3).

Thanks to constant technological advances, used in the different phases of cultivation of lamb's lettuce such as sowing, planting, protection, and harvesting it is now possible to produce this salad vegetable out of season. This means that spring cultivation of corn salad and all year round consumption of this delicate salad vegetable is also possible.

The seed of *Valerianella locusta* as it is sown or marketed is botanically not a seed, but a ridged fruit having 3 locules or chambers, of which only one is fertile and holds a single seed containing the embryo and hardly or no endosperm. The other two locules are sterile and empty. The empty locules or 'air chambers' allow the fruit to float.

When corn salad is grown for seed production, the plants stay on the field until they flower and form seeds. One plant can produce 600-700 seeds. The seeds are very dehiscent and thus the harvest of the plants or stems carrying the seeds occurs before the seeds are fully mature. The drying process occurs at another location that is dry and well ventilated.

Most of the corn salad for commercial vegetable production is sown mechanically. The fruits must have a size that fits in a specific calibre of the machine. The average size of fruits produced on corn salad plants varies depending on the variety and on the season. Fruits coming from winter cultivars for example are in general smaller than fruits coming from spring cultivars. The calibre of the machines has to be adjusted regularly to match with the fraction size that is used. A certain percentage of produced seed is not suitable for machine sowing because the size is too large or too small and it is difficult to adjust the machines accordingly.

Fruits coming from cultivated corn salad have different sizes, even if they are harvested from the same variety. Seeds, or actually fruits, that are intended for commercial marketing are cleaned to remove the sizes that are either too small or too large. The remainder is fractionalized into size categories with differences of 0.25 mm, which results in categories of 1.5-1.75 mm., 1.75-2.0 mm., etc. Certain fractions are considered too large, and others too small, which fractions are usually rejected. The fractionalizing is required so that a certain batch of seeds that is bought by a grower can be used in the sowing machine as a whole. The major portion of the size of the whole corn salad fruits is determined by the (empty) air chambers; the fractionalizing considers the size of the fruit as a whole.

Due to the large 'useless' portion of corn salad fruits, packing of corn salad fruits for vegetable growers is not very efficient. When the size of the fruits could be reduced and be more conform with the actual size of the seeds, less volume per fruit would be required. It can be estimated that probably only half or less of the packaging volumes would be needed if the size of the air chambers of corn salad could be reduced. This reduction in volume saves transporting and storage costs.

Germination of commercially available corn salad is considered not to be very fast, not very high, and not very uniform. In essence, the 'seed vigor' or 'germination energy', which both encompass uniformity and speed of germination, is not up to expected standards. Especially after fractionalizing, which results in a batch of fruits that is more uniform in size, the results are disappointing. The improved uniformity in size is expected to relate also to an increase in uniformity related to germination. Non-uniformity results in corn salad plants of different starting sizes, which in the end gives irregular mature plant sizes. This logically has a negative impact on the yield and therefore sales value that can be obtained by a grower.

Citation or identification of any document in this application is not an admission that such document is available as prior art to the present invention.

SUMMARY OF THE INVENTION

During research that led to the present invention the variation in seed size within a batch of fruits of the same fraction size was investigated. Five commercially available corn salad varieties were divided into fractions, and the length of the seeds was measured. Analysis of the measurements indicated that after fractionalizing the fruits, the lengths of the actual seeds between those fractions was not significantly different (Table 1).

The standard deviations of seed sizes within a certain fraction were rather high. Especially for the varieties that contained more differently sized fractions, and therefore a higher average fraction size of the whole variety, the standard deviations were high. It was concluded that fractionalizing of the fruit size does not result in a corresponding fractionalizing of the seed size (FIG. 1).

TABLE 1

Seed size in mm. for different fractions, measured from X-ray photograph

| | Variety | fraction | Norm. Av. mm | Norm. SD |
|---|---|---|---|---|
| 1 | Gala | 1.75 | 2.02 | 0.15 |
| 1 | Gala | 2.00 | 2.18 | 0.10 |
| 1 | Gala | 2.25 | 2.27 | 0.12 |
| 2 | Granon | 1.75 | 1.90 | 0.18 |
| 2 | Granon | 2.00 | 2.07 | 0.13 |
| 2 | Granon | 2.25 | 2.26 | 0.11 |
| 2 | Granon | 2.50 | 2.18 | 0.10 |
| 3 | Pulsar | 2.75 | 2.76 | 0.21 |
| 3 | Pulsar | 2.50 | 2.94 | 0.21 |
| 3 | Pulsar | 2.25 | 2.69 | 0.24 |
| 3 | Pulsar | 2.00 | 2.67 | 0.25 |
| 3 | Pulsar | 1.75 | 2.59 | 0.22 |
| 4 | Toendra | 1.75 | 2.58 | 0.26 |
| 4 | Toendra | 2.00 | 2.83 | 0.32 |
| 4 | Toendra | 2.25 | 2.76 | 0.24 |
| 4 | Toendra | 2.50 | 2.81 | 0.18 |
| 4 | Toendra | 2.75 | 2.93 | 0.21 |
| 5 | Trophy | 1.75 | 2.32 | 0.24 |
| 5 | Trophy | 2.00 | 2.27 | 0.17 |
| 5 | Trophy | 2.25 | 2.45 | 0.19 |
| 5 | Trophy | 2.50 | 2.60 | 0.11 |
| 5 | Trophy | 2.75 | 2.84 | 0.17 |
| | | | mm | mm |

There is a high variation of seed size within a certain fruit size fraction. This variation in seed size can lead to irregular and/or slow germination even within a certain fraction, since uniformity in germination is assumed to be determined more by the size of the seeds, or even of the embryo's, than by the size of the fruits as a whole. The high variation of seed size is expected to be correlated with a high variation of embryo size. A seed of the botanical family Valerianacea is almost completely filled with a large embryo which may comprise a hypocotyl and cotyledons, and hardly, usually just one layer of cells, or no endosperm is present. The seed size and embryo size of species within the Valerianaceae, and especially within the genus *Valerianella* such as *Valerianella locusta*, are therefore highly correlated.

Since the size of the real seed and/or of the embryo is expected to contribute more to the germination than the size of the fruits, the uniformity of fruits after fractionalizing probably has a lower than expected impact on the uniformity and/or the speed of the germination. The uniformity of prior art corn salad fruits after fractionalizing thus has a lower than expected impact on the germination energy.

It is the object of the present invention to provide corn salad fruits with an improved germination.

According to the present invention a new type of fruits produced by a *Valerianella locusta* plant was developed which fruits have a significantly smaller fruit width and a higher length/width ratio. It was surprisingly found that this new fruit type leads to a faster and/or more uniform germination.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of *Valerianella locusta* 09.10211 that comprise the genetic determinant of the invention which leads to a fruit width smaller than 1.7 mm, and/or a length/width ratio of the fruit higher than 1.2, and/or an improved germination were deposited with NCIMB Ltd, Ferguson Building, Craibstone Estate, Bucksburn, Aberdeen AB21 9YA, UK on May 7, 2012 under deposit accession number NCIMB 42007.

The Deposits with NCIMB Ltd, under deposit accession number NCIMB 42007 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

A) Fruits of *V. locusta* having two large air chambers (sterile locules).

B) The air chambers enclose the seed (fertile locule) from both sides.

C) *V. locusta* fruit according to the invention

D) The two sterile locules of a fruit of the invention are diminished. In this picture they are located at one side; they are optionally fused.

Figure 3:
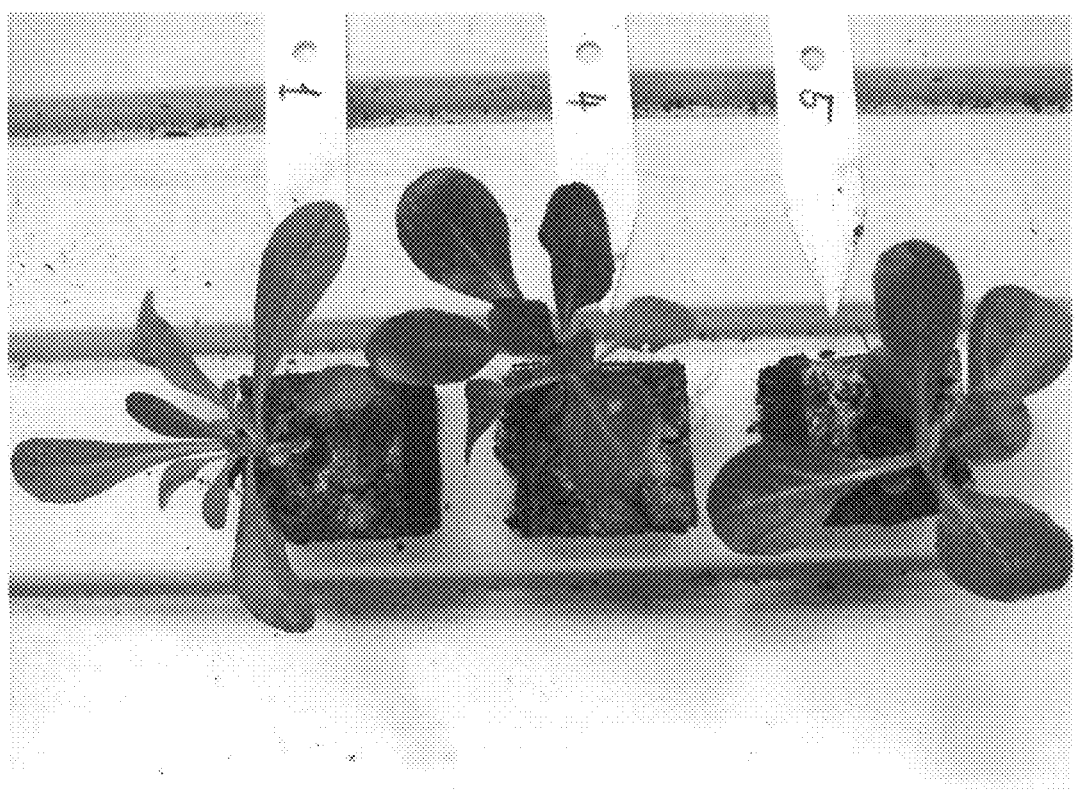

FIG. 3: Pictures of the plant habit of cultivated *V. locusta* corn salad plants as compared to *V. carinata* plants.

No. 1: plant habit of *V. carinata*

No. 4: plant habit of cultivated *V. locusta*-deposit NCIMB 42007

No. 5: plant habit of cultivated *V. locusta* 'Cirilla'

DETAILED DESCRIPTION OF THE INVENTION

The invention thus provides a corn salad fruit of the species *Valerianella locusta* characterised by a fruit width which is smaller than 1.7 mm, which fruit width is determined by a genetic determinant which is as found in fruits of which a representative sample was deposited under accession number NCIMB 42007.

In one embodiment, the invention provides a corn salad fruit of the species *Valerianella locusta*, characterised by a length/width ratio of the fruits which is higher than 1.2, which length/width ratio is determined by a genetic determinant which is as found in fruits of which a representative sample was deposited under accession number NCIMB 42007.

A corn salad fruit of the species *Valerianella locusta* of the invention is preferably characterised by a fruit width which in order of increased preference is smaller than 1.7 mm, 1.6 mm, 1.5 mm, 1.4 mm, 1.3 mm, 1.2 mm, 1.1 mm, 1.0 mm, 0.9 mm, and/or a length/width ratio of the fruits which in order of increased preference is higher than 1.2, 1.3, 1.4, 1.5, 1.6, 1.7, 1.8, 1.9, which fruit width and/or length/width ratio are/is determined by a genetic determinant which is as found in, or is obtainable from, fruits of which a representative sample was deposited under accession number NCIMB 42007, or is equivalent to the said genetic determinant in NCIMB 42007.

The fruit width smaller than 1.7 mm and the length/width ratio of the fruits higher than 1.2 are phenotypic markers of seeds that show an improved germination. In this application fruits that are indicated to have a fruit width smaller than 1.7 mm and/or a length/width ratio of the fruits higher than 1.2 are fruits that also show a better germination.

The genetic determinant of the invention that results in a fruit width smaller than 1.7 mm, and/or a length/width ratio of the fruit higher than 1.2, and/or an improved germination, inherits in a recessive manner, and is determined by a single gene or by closely linked genes that inherit as one single recessive gene (Example 1, Example 5). The genetic determinant expresses a fruit width smaller than 1.7 mm, and/or a length/width ratio of the fruit higher than 1.2, and/or an improved germination when it is present in homozygous stage.

Figure 1:
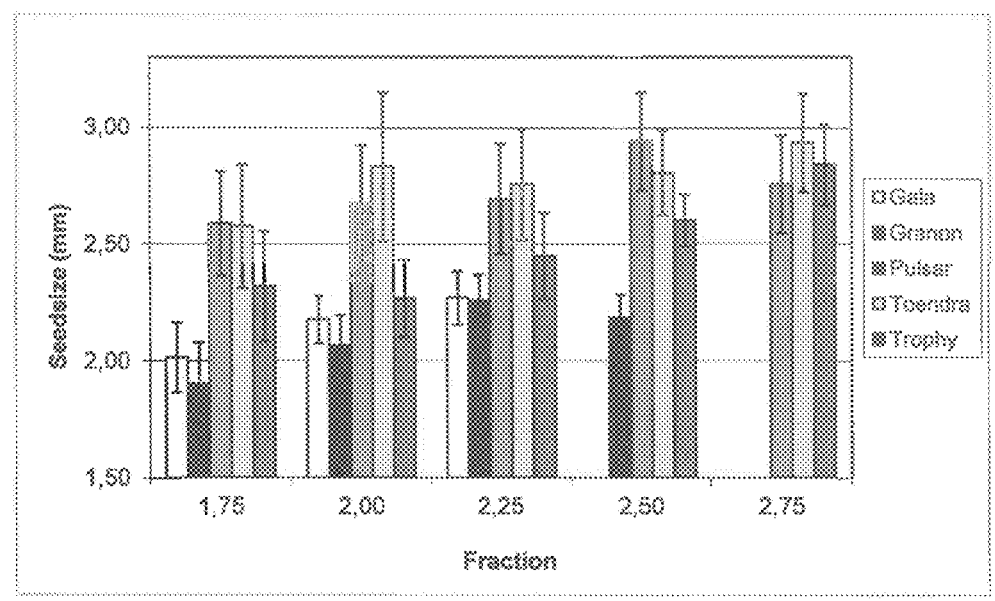
FIG. 1: Seed size per fraction of five commercially available corn salad varieties.
Figure 2:
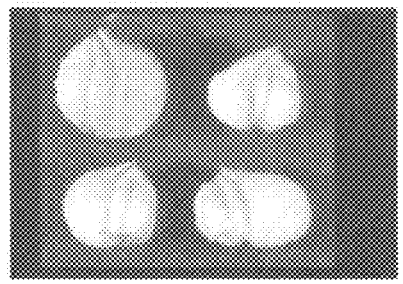
FIG. 2: Pictures of fruits of corn salad.
Figure 2:
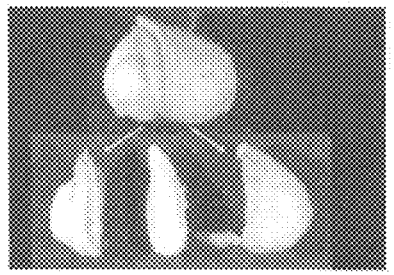
Figure 2:
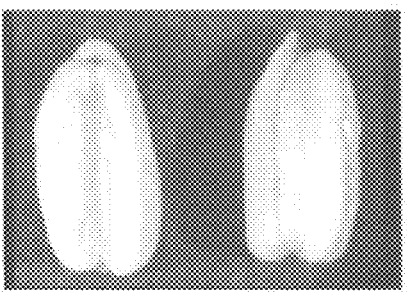
Figure 2:
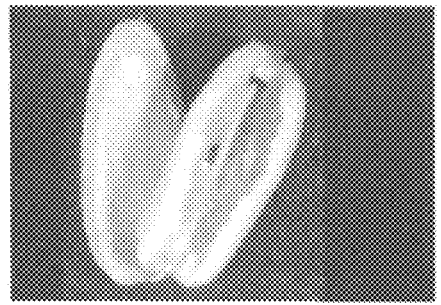

Fruits of *Valerianella locusta* botanically may comprise three elements. One part, that is developed from one locule, is the seed, which is primarily filled with the embryo. This fertile locule is rather narrow. The width of the whole fruit, which can be perceived to be roundish, is largely determined by the two other, sterile, empty locules or 'air chambers' on the sides (FIGS. 2A and B). The size of the total fruit can vary and usually fruits are fractionalized to get a better uniformity of the size.

Fruits of another *Valerianella* species, *Valerianella carinata*, have a different morphology. They also have three locules, of which only one is fertile and contains the seed. The other two sterile locules however are strongly diminished and therefore much smaller than the sterile locules of *V. locusta*. The size of a complete *V. carinata* fruit is mainly determined by the fertile locule, i.e. the seed. The shape of the whole fruit of *V. carinata* is elongated and not round.

The shape of the fruit is a very essential characteristic within the genus *Valerianella*, as it is one of the main morphological characteristics by which the different species are taxonomically distinguished. The fruit type of *V. locusta*, which may comprise the two air-filled empty locules, are typical for this species. No other fruit types are known within the species *Valerianella locusta*.

An overview of the different fruit shapes of five important *Valerianella* species can be found at the 'Species Fact sheet' pdf of the *Valerianella rimosa* page of the web site of the National Museum Wales.

'Corn salad fruit' or 'fruit' as used herein is the mature corn salad seed combined with one or two sterile locules that are optionally empty or filled with air and that are optionally fused. In some instances the fruit is referred to as a 'seed'. When a 'seed' is sown it obviously may comprise the whole fruit. For measurements as done herein however the reference to 'seed' only indicates the fertile locule that is separated from the sterile locules. The 'embryo' is contained within the seed.

During the development of the present invention the approach was to introgress the shape of *V. carinata* fruits into *V. locusta*. Crosses between the two species are difficult to make, but an attempt was done to make a cross between *V. locusta* and *V. carinata*, which succeeded. Some interspecific plants were regenerated from the cross. The interspecific F1 hybrid plants had morphological characteristics from both species. The fruits that were formed on the interspecific F1 plants had the fruit shape and fruit type of *V. locusta*.

F1 plants were selfed, and through repeated selection and selfing a plant was obtained that had all the morphological characteristics of *V. locusta* apart from the fruit shape which was introgressed from *V. carinata* (FIGS. 2C and D). This novel plant was selfed and bulk-massed after which sufficient seeds for testing were obtained. Progeny of this plant in which the trait of the invention was uniformly present was produced and given the code 09.10211, which was used for the deposit (Example 1).

Fruit sizes of plants of the invention, the *V. carinata* parent and the *V. locusta* parent were measured and compared. In addition, the fruit sizes of five commercial corn salad varieties of different average sizes were measured. Although the lengths of the fruits of the invention were rather small, no significant difference for length with other small-sized corn salad varieties was determined. The standard deviation also did not differ significantly from those of regular corn salad varieties (Table 2).

The width of batches of fruits of the same accessions was also measured. Here the result was substantially different, as the width of fruits of the invention was considerably smaller than the width of the fruits of *V. locusta* fruits that do not have the genetic determinant of the invention. The significantly smaller fruit width combined with an approximately similar fruit length, results in a length/width ratio of *V.*

*locusta* fruits of the invention that is much higher than the length/width ratio of *V. locusta* fruits that do not have the genetic determinant of the invention (Table 2).

In one embodiment the fruit width of a *V. locusta* fruit of the invention in order of increased preference is smaller than 1.7 mm, 1.6 mm, 1.5 mm, 1.4 mm, 1.3 mm, 1.2 mm, 1.1 mm, 1.0 mm, 0.9 mm.

In one embodiment the length/width ratio of the fruit size of a *V. locusta* fruit of the invention in order of increased preference is higher than 1.2, 1.3, 1.4, 1.5, 1.6, 1.7, 1.8, 1.9.

TABLE 2

Fruit sizes and standard deviations of corn salad

| | Width | Length | Ratio |
|---|---|---|---|
| 1. *V. carinata* | 0.91 | 1.75 | 1.9 |
| 2. *V. locusta* - invention | 1.00 | 1.90 | 1.9 |
| 3. *V. locusta* 'Cirilla' | 2.07 | 1.98 | 1.0 |
| 4. *V. locusta* 'Gala' | 1.71 | 1.98 | 1.2 |
| 5. *V. locusta* 'Granon' | 2.03 | 2.02 | 1.0 |
| 6. *V. locusta* 'Pulsar' | 2.73 | 2.80 | 1.0 |
| 7. *V. locusta* 'Toendra' | 2.71 | 2.82 | 1.0 |
| 8. *V. locusta* 'Trophy' | 2.41 | 2.59 | 1.1 |

| | SD Width | Length |
|---|---|---|
| 1. *V. carinata* | 0.12 | 0.14 |
| 2. *V. locusta* - invention | 0.14 | 0.18 |
| 3. *V. locusta* 'Cirilla' | 0.4 | 0.19 |
| 4. *V. locusta* 'Gala' | 0.43 | 0.13 |
| 5. *V. locusta* 'Granon' | 0.27 | 0.21 |
| 6. *V. locusta* 'Pulsar' | 0.39 | 0.20 |
| 7. *V. locusta* 'Toendra' | 0.42 | 0.27 |
| 8. *V. locusta* 'Trophy' | 0.49 | 0.28 |

The invention thus relates to a more uniform distribution in fruit size and/or fruit width of *V. locusta* fruits of the invention as compared to *V. locusta* fruits that do not have the genetic determinant of the invention.

The standard deviation (SD) of the width of a batch of *V. locusta* fruits of the invention is significantly smaller than the SD of the width of other batches of *V. locusta* fruits. The SD of the width of a batch of *V. locusta* fruits that does not have the trait of the invention is very high, which indicates a lot of variation for the fruit width in such a batch. The SD for fruit length in *V. locusta* fruits that do not have the trait of the invention is generally much smaller than the SD for fruit width of those same fruits. It can therefore be deduced that the variation in fruit size as a whole, which is related to both the fruit length and the fruit width, is largely determined by the variation in fruit width.

An increase in the uniformity of fruit width, represented as a decrease in the standard deviation of fruit width, will therefore result in an increase in the uniformity of fruit size. An increase in the uniformity of fruit width results in a more uniform distribution of fruit width, which results in a more uniform distribution of fruit size.

Preferably, the standard deviation of the fruit width of a batch of *V. locusta* fruits of the invention in order of increased preference is smaller than 0.20, smaller than 0.18, smaller than 0.16, smaller than 0.14.

In one embodiment the invention relates to a corn salad fruit wherein a batch of *V. locusta* fruits of a certain fraction size which may comprise the genetic determinant of the invention shows a more uniform distribution of embryo size as compared to a batch of *V. locusta* fruits of a certain fraction size not having the genetic determinant.

In one embodiment the invention relates to a corn salad fruit wherein a batch of *V. locusta* fruits of a certain fraction size, carrying the genetic determinant of the invention, further has a significantly larger embryo size as compared to the embryo size of a batch of *V. locusta* fruits of a certain fraction size not having the genetic determinant. Suitably the compared fraction sizes are the same.

Fruits of the invention were determined to have a higher uniformity in fruit size, especially for fruit width. Further research was done to determine if the uniformity in fruit size was related to uniformity of seed size and/or uniformity of embryo size of fruits of the invention.

Embryo sizes within a certain fraction size of fruits of the invention were measured, and the variation of embryo sizes within this fraction was determined. The same was done for fraction sizes of the *V. locusta* parent 'Cirilla' that was used in developing the trait of the invention, which did not carry the genetic determinant of the invention, and for the *V. carinata* parent (Table 3).

TABLE 3 embryo sizes corn salad (mm).

| | fraction | | | | |
|---|---|---|---|---|---|
| | *V. locusta* of the invention 1.5-1.75 | *V. carinata* | *V. locusta* 'Cirilla' 1.5-1.75 | *V. locusta* 'Cirilla' 2.0-2.25 | *V. locusta* 'Cirilla' 2.25-2.5 |
| average | 2.03 | 1.97 | 1.57 | 1.71 | 1.75 |
| st. dev. | 0.14 | 0.14 | 0.18 | 0.20 | 0.22 |

From the analysed data it was established that within a certain fraction, the variation in embryo size as expressed by the standard deviation was significantly smaller for a fraction of fruits from *V. locusta* fruits of the invention, than for the embryo sizes of *V. locusta* fractions not carrying the genetic determinant of the invention. This means that within a certain fraction the uniformity in embryo size is increased in *V. locusta* fruits of the invention.

In addition, the average size of the embryo's of a fruit size fraction of *V. locusta* fruits of the invention was increased as compared to the size of embryo's of the same fraction from *V. locusta* fruits not carrying the genetic determinant of the invention.

In one embodiment the standard deviation of the embryo size of a batch of fruits of a certain fraction size in order of increased preference is smaller than 0.18, 0.17, 0.16, 0.15, 0.14.

In a further embodiment a batch of fruits of the invention used to determine the standard deviation of the embryo size is a batch of one fraction size. The different fraction sizes are commonly used and well known to the skilled person. Suitably a fraction size of 1.5-1.75 is used to determine the standard deviation for embryo size.

In one embodiment a batch of fruits used to determine the standard deviation of the embryo size contains at least 60 fruits.

The invention also relates to corn salad fruits of the species *V. locusta*, wherein as a result of the presence of the genetic determinant of the invention in the *V. locusta* genome, a batch of *V. locusta* fruits of a certain fraction size has an improved germination as compared to a batch of *V. locusta* fruits of a certain fraction size not carrying the genetic determinant.

In a further embodiment the batches of fruits of the invention and of *V. locusta* fruits not carrying the genetic determinant of the invention that are compared for germination are of the same fraction size.

A better germination or an improved germination as used herein is a germination that is faster and/or a germination that is more uniform and/or a germination that has a higher germination energy.

A uniform germination means that the number of days in which a certain percentage of seeds germinates is low. It is possible that initially no seeds germinate for several days, but if after those days a high percentage of seeds germinates within a low number of days, the germination is still uniform. Counting of the number of days therefore starts when the first seed has germinated. 'More uniform' means that the number of days is lower than a control.

A fast germination means that a high percentage of seeds germinates within a short period after sowing. The counting of the period therefore starts at the day of sowing. 'Faster germination' means that the period is shorter than a control.

Comparison of germination related aspects as performed herein is preferably done between fruits or seeds that have not been subject to any treatment that improves the germination, such as chemical or physiological treatments. Comparison of germination is preferably also done on fruits or seeds that are of a comparable age, since germination is known to be reduced after seeds have been stored for a certain period of time. Most preferably batches of seeds are compared that were produced in the same season. Comparison of germination should always be done at the same time under the same growing conditions.

'Germination energy' as used herein is the percentage of seeds that germinates within a certain indicated period, which period is the 'energy period', under optimum or stated conditions. When the 'energy period' is short, a high 'germination energy' relates to fast germination. When the 'energy period' is short, a high 'germination energy' relates to uniform germination. The combination of a high 'germination energy' within a short 'energy period' results in a fast and uniform germination. A fast and uniform germination means that the 'seed vigor' is high.

A high percentage of seeds in order of increased preference is 80%, 85%, 90%, 94%, 96%, 98%, 100%.

A batch of corn salad fruits of the invention having a certain fraction size was compared for germination to a control batch of *V. locusta* corn salad fruits of the same fraction size and to a control batch of *V. carinata* fruits of the same fraction size.

Both controls were used to develop the fruits of the invention. It was however highly surprisingly found that the germination of the fruits of the invention was remarkably increased for speed as compared to both populations of the control plants. The fruits of the invention had a fast germination. It was also surprisingly found that the germination of fruits of the invention was improved for uniformity when compared to the controls. The fruits of the invention had a more uniform germination. Fruits of the invention had a faster and more uniform germination, and were therefore highly improved in germination.

The *V. carinata* fruits, that have the same fruit type as the *V. locusta* fruits of the invention, had a slow and rather poor germination. The fruit type on itself therefore does not result in a good germination.

Moreover, the *V. carinata* fruits had shown to have the same embryo size as fruits of the invention. However, the embryo size on itself does not result in a good germination. The combination of fruit type and embryo size on themselves, without having been introgressed in a *V. locusta* background, does not result in a good germination.

The new fruit type which results in an increased and more uniform embryo size in a certain *V. locusta* fraction size has surprisingly expressed an improved germination over a *V. locusta* batch of the same fraction size.

A batch of control *V. locusta* fruits of the same fraction size as the tested batch of fruits of the invention was remarkably slower in germination. The germination was spread over a longer period of time, and was therefore less uniform. The new fruits that have introgressed the new fruit type within *V. locusta* surprisingly outperform both species for germination speed, germination uniformity, and/or germination energy (Table 4).

It was therefore surprisingly determined that the decreased fruit width which is smaller than 1.7 mm and/or the higher length/width ratio of the fruits of the invention which is higher than 1.2 can be used as a phenotypic marker for an improved germination in fruits that have the genetic determinant of the invention. The assessment of fruit size is clearly much easier to perform than a germination assay. This makes the development of corn salad with an improved germination as a result of the genetic determinant of the invention a very useful approach in breeding.

The improved germination aspects result in a substantial improvement for the mechanical sowing of corn salad seeds that can result in higher, more stable, and more uniform yields and better profits for the growers.

TABLE 4

Germination energy

Table 4a: Germination of plants of the invention (4.) as compared to its parents (1. and 3.). 200 fruits were sown. Before day 4, no germination took place.

| | 4 DAS | | 5 DAS | | 6 DAS | | 7 DAS | |
|---|---|---|---|---|---|---|---|---|
| | fruits | total % | fruits | total % | fruits | total % | fruits | total % |
| 1. | 48 | 24% | 102 | 51% | 135 | 67.50% | 166 | 83% |
| 3. | 90 | 45% | 161 | 80.50% | 179 | 89.50% | 187 | 93.50% |
| 4. | 128 | 64% | 188 | 94% | 197 | 98.50% | 200 | 100% |

Table 4b: Germination of plants of the invention (4.), as compared to its parents (1., 2., and 3.) and commercially available corn salad varieties (5. and 6.). 200 fruits were sown. After 10 days, no additional plants germinated. Before day 4, no germination took place.

| | 4 DAS | | 5 DAS | | 6 DAS | | 7 DAS | | 8 DAS | | 9 DAS | | 10 DAS | |
|---|---|---|---|---|---|---|---|---|---|---|---|---|---|---|
| | fruits | total % | fruits | total % | fruits | total % | fruits | total % | fruits | total % | fruits | total % | fruits | total % |
| 1. | 54 | 27% | 133 | 66.5% | 166 | 83% | 172 | 86% | 182 | 91% | 188 | 94% | 190 | 95% |
| 2. | 32 | 16% | 108 | 54% | 126 | 63% | 154 | 77% | 167 | 83.5% | 180 | 90% | | |
| 3. | 39 | 19.5% | 138 | 69% | 146 | 73% | 176 | 88% | 184 | 92% | 191 | 95.5% | | |

TABLE 4-continued

| | | | | | | Germination energy | | | | | | | |
|---|---|---|---|---|---|---|---|---|---|---|---|---|---|
| 4. | 103 | 51.5% | 169 | 84.5% | 195 | 97.5% | 200 | 100% | | | | | |
| 5. | 0 | 0% | 33 | 16.5% | 112 | 56% | 143 | 71.5% | 158 | 79% | 166 | 83% | 168 | 84% |
| 6. | 8 | 4% | 143 | 71.5% | 193 | 96.5% | 196 | 98% | 200 | 100% | | | | |

1: *V. carinata* fraction size 1.5-1.75 mm
2: *V. locusta* 'Cirilla' fraction size <1.5 mm
3: *V. locusta* 'Cirilla' fraction size 1.5-1.75 mm
4: *V. locusta* 09.10211 fraction size 1.5-1.75 mm
5: *V. locusta* 'Pulsar' fraction size 2.5-2.75 mm
6: *V. locusta* 'Gala' fraction size 1.75-2.0 mm
DAS: Days after sowing In one embodiment the germination of a batch of *V. locusta* fruits of a certain fraction size, having the genetic determinant of the invention, in order of increased preference is
  higher than 45%, 46%, 47%, 48%, 49%, 50%, 51% at 4 days after sowing, and/or
  higher than 81%, 82%, 83%, 84% at 5 days after sowing, and/or
  higher than 97% at 6 days after sowing, and/or
  higher than 98%, 99% at 7 days after sowing.

In one embodiment the germination of a batch of *V. locusta* fruits of a certain fraction size, carrying the genetic determinant of the invention, in order of increased preference is at least
  3% higher, 6% higher, 10% higher, 13% higher, 16% higher, 19% higher at 4 days after sowing as compared to a batch of parent fruits of *V. locusta* of a certain fraction size not carrying the genetic determinant, and/or at least
  3% higher, 5% higher, 7% higher, 9% higher, 11% higher, 13% higher at 5 days after sowing as compared to a batch of parent fruits of *V. locusta* of a certain fraction size not carrying the genetic determinant, and/or at least
  2% higher, 4% higher, 6% higher, 8% higher, 9% higher at 6 days after sowing as compared to a batch of parent fruits of *V. locusta* of a certain fraction size not carrying the genetic determinant, and/or at least
  2% higher, 4% higher, 5% higher, 6% higher at 7 days after sowing as compared to a batch of parent fruits of *V. locusta* of a certain fraction size not carrying the genetic determinant.

In one embodiment the germination of a batch of *V. locusta* fruits of a certain fraction size, carrying the genetic determinant of the invention, in order of increased preference is at least
  3% higher, 6% higher, 10% higher, 13% higher, 16% higher, 19% higher at 4 days after sowing as compared to a batch of fruits of *V. locusta* of a certain fraction size not carrying the genetic determinant, and/or at least
  3% higher, 5% higher, 7% higher, 9% higher, 11% higher, 13% higher at 5 days after sowing as compared to a batch of fruits of *V. locusta* of a certain fraction size not carrying the genetic determinant, and/or at least
  1% higher at 6 days after sowing as compared to a batch of fruits of *V. locusta* of a certain fraction size not carrying the genetic determinant, and/or at least
  2% higher at 7 days after sowing as compared to a batch of fruits of *V. locusta* of a certain fraction size not carrying the genetic determinant.

In one embodiment the germination of a batch of *V. locusta* fruits of a certain fraction size, having the genetic determinant of the invention, germinates in four days, and/or is germinated to its full potential at 7 days after sowing. When a batch germinates in four days it means that the germination period from the first germinating seed till no more seeds germinate is four days. Germinated to its full potential means that no more seeds will germinate after that day.

It was also determined that the germination period of a batch of *V. locusta* fruits of a certain fraction size, having the genetic determinant of the invention, is at least one day shorter than the germination period of a batch of *V. locusta* fruits of a certain fraction size not having the genetic determinant. When compared to parent fruits without the genetic determinant, the germination period of a batch of fruits of a certain fraction size having the genetic determinant of the invention is at least one day shorter, preferably two days shorter.

Comparison of germination as described above was performed on batches of 200 fruits. Sowing was done on filter paper, and the trial was kept at a temperature of 15° C., and a relative humidity of 100%. The germination trial was kept in dark conditions for 24 hours/day until the end, when no more additional germination took place.

It was furthermore found that the fruits of the invention that have an improved germination result in plants with a higher biomass at harvest stage as compared to plants resulting from *V. locusta* fruits, optionally of the same fraction size, not carrying the genetic determinant of the invention.

Plants resulting from fruits of the invention of a certain fraction size were compared with plants resulting from *V. locusta* fruits of the same fraction size that did not carry the genetic determinant of the invention. It was surprisingly found that the plants of the invention have a much higher biomass, and therefore a higher yield, than the plants not containing the genetic determinant of the invention (Table 5). All plants were sown and harvested at the same time. This means that the plant vigor of plants of the invention is significantly improved over regular *V. locusta* plants, which is an additional major advantage for corn salad growers.

TABLE 5

| Plant vigor - average of 20 plants | |
|---|---|
| | Biomass (gram) rosette plant at harvesting stage |
| 1. *V. carinata* (1.5-1.75) | 3.8 g |
| 2. *V. locusta* 'Cirilla' (1.5-1.75) | 2.6 g |
| 3. *V. locusta* 09.10211(1.5-1.75) | 4.2 g |

In a preferred embodiment the average percentage of empty seeds in fruits of the invention is suitably less than 10%, preferably less than 7%, more preferably less than 5%, even more preferably less than 3%, most preferably less than 1%. The average percentage can be calculated for a batch of fruits of at least 40, optionally at least 60, at least 100, or batches of a higher number of fruits.

When corn salad seeds of the invention were further analysed, it was surprisingly found that the percentage of empty seeds was significantly reduced as compared to a control *V. locusta* variety. The control variety is preferably an isogenic variety, i.e. they are genetically the same or very close, apart from the genetic determinant of the invention. The control can also be a variety or line that was used as a parent in developing *V. locusta* fruits having the genetic determinant of the invention. The corn salad variety *V. locusta* is a parent variety used in developing the plants of the deposit that was done under accession NCIMB 42007. A significant reduction in empty seeds, i.e. seeds that do not contain an embryo and therefore cannot germinate, results in a reduction in losses during seed cleaning. A lower percentage of empty seeds also results in a higher germination and ultimately a higher yield.

The average size of the fruits of the invention produced by a *Valerianella locusta* plant is smaller than the size of fruits of known cultivated corn salad plants. However, the variation in size between seasons is lower than for *V. locusta* fruits that do not carry the genetic determinant of the invention. The average fruit size can be measured in several ways which are well known by the person skilled in the art, for example with a metric ruler, using a dual camera system and image analysis with a specific algorithm.

The invention further relates to fruits of corn salad of the species *V. locusta* that may comprise air chambers that are smaller than the air chambers of the fruits of *Valerianella locusta* not having the genetic determinant of the invention.

The genetic determinant of the invention can be introgressed into other corn salad plants. Such plants that carry the genetic determinant as found in the deposited seeds of NCIMB 42007 are also plants of the invention.

"Introgression" as used herein is intended to mean introduction of a genetic determinant into a plant not carrying the genetic determinant by means of crossing, and selection for the trait in the first generation in which the trait becomes visible.

It is clear that the parent that provides the genetic determinant that results in a plant of the invention is not necessarily a plant grown directly from the deposited seeds. The parent can also be a progeny plant from the seed, or a progeny plant from seeds that are identified to have the genetic determinant of the invention by other means.

A *Valerianella locusta* plant of the invention is a plant that is grown from *V. locusta* fruits carrying the genetic determinant of the invention, or a *V. locusta* plant that produces fruits carrying the genetic determinant of the invention. A *Valerianella locusta* plant of the invention is preferably a cultivated corn salad plant.

The invention further relates to a cell of a *V. locusta* plant grown from or producing a fruit of the invention. Such cell may be either in isolated form or may be part of the complete *V. locusta* plant or parts thereof and then still constitutes a cell of the invention because such a cell harbors in its genetic constitution the genetic information that leads to the characteristics that define the *V. locusta* plant of the invention. Each cell of *V. locusta* plants of the invention carries the genetic determinant that leads to phenotypic expression of said trait. Such a cell of the invention may also be a regenerable cell that can be used to regenerate a new *V. locusta* plant producing a fruit of the invention.

The invention also relates to tissue of a plant as claimed. The tissue can be undifferentiated tissue or already differentiated tissue. Undifferentiated tissues are for example stem tips, anthers, petals, pollen and can be used in micropropagation to obtain new plantlets that are grown into new plants of the invention. The tissue can also be grown from a cell of the invention.

The invention also relates to progeny of the plants, cells, tissues and seeds of the invention. Such progeny can in itself be plants, cells, tissues or seeds.

As used herein the word "progeny" is intended to mean the first and all further descendants from a cross with a plant grown from a fruit of the invention that may comprise the genetic determinant that leads to the trait of a fruit width smaller than 1.7 mm, and/or a length/fruit ratio of the fruit higher than 1.2, and/or an improved germination of a batch of fruits of a certain fraction size as compared to a batch of *V. locusta* fruits of a certain fraction size not having the genetic determinant. Progeny of the invention are descendants of any cross with a plant of the invention or a plant grown from a fruit of the invention that carries the genetic determinant that leads to the trait of the invention.

"Progeny" also encompasses plants that carry the genetic determinant that causes the trait of a fruit width smaller than 1.7 mm, and/or a length/width ratio of the fruit higher than 1.2, and/or an improved germination of a batch of fruits of a certain fraction size as compared to a batch of *V. locusta* fruits of a certain fraction size not having the genetic determinant, which plants are obtained from other plants or progeny of plants of the invention by vegetative propagation or multiplication.

The invention relates to propagation material suitable for producing a plant having the genetic determinant of the invention. The invention thus further relates to seed of the claimed plant and to parts of the plant that are suitable for sexual reproduction. Such parts are for example selected from the group consisting of microspores, pollen, ovaries, ovules, embryo sacs and egg cells. In addition, the invention relates to parts of the plant that are suitable for vegetative reproduction, in particular cuttings, roots, stems, cells, and protoplasts.

According to a further aspect thereof the invention provides a tissue culture of the claimed plant. The tissue culture may comprise regenerable cells. Such tissue culture can be derived from leaves, pollen, embryos, cotyledons, hypocotyls, meristematic cells, roots, root tips, anthers, flowers, fruits, seeds and stems. The tissue culture can be regenerated into a plant carrying the genetic determinant of the invention. Suitably a regenerated plant expresses the phenotype of a fruit width smaller than 1.7 mm, and/or a length/width ratio of the fruit higher than 1.2.

The invention furthermore relates to hybrid seed and to a method of producing hybrid seed which may comprise crossing a first parent plant with a second parent plant and harvesting the resultant hybrid seed. Said first parent plant or said first parent plant and said second parent plant homozygously have the genetic determinant that leads to the trait of a fruit width smaller than 1.7 mm, and/or a length/width ratio of the fruit higher than 1.2, and/or an improved germination of a batch of fruits of a certain fraction size as compared to a batch of *V. locusta* fruits of a certain fraction size not having the genetic determinant. The resulting hybrid plant is a plant of the invention.

In one embodiment, the invention relates to *V. locusta* plants of the invention that carry the genetic determinant of the invention which leads to the trait of a fruit width smaller than 1.7 mm, and/or a length/width ratio higher than 1.2, and/or an improved germination of a batch of fruits of a certain fraction size as compared to a batch of *V. locusta* fruits of a certain fraction size not having the genetic determinant, and that have acquired said determinant by introduction of the genetic determinant that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which the genetic determinant of the invention is acquired is formed by plants grown from seeds of which a representative sample was deposited under accession number NCIMB 42007, or from the deposited seeds NCIMB 42007, or from sexual or vegetative descendants thereof, or from another source which may comprise the genetic determinant that leads to the trait of a fruit width smaller than 1.7 mm, and/or a length/width ratio of the fruit higher than 1.2, and/or an improved germination of a batch of fruits of a certain fraction size as compared to a batch of *V. locusta* fruits of a certain fraction size not having the genetic determinant, or from a combination of these sources.

In a preferred embodiment, the invention relates to non-transgenic *Valerianella locusta* plants. The source for acquiring the genetic determinant of the invention, to obtain a plant of the invention that has the trait of a fruit width smaller than 1.7 mm, and/or a length/width ratio of the fruit higher than 1.2, and/or an improved germination of a batch of fruits of a certain fraction size as compared to a batch of *V. locusta* fruits of a certain fraction size not having the genetic determinant, is suitably a *V. locusta* plant that carries the genetic determinant of NCIMB 42007, or alternatively a plant of a *Valerianella* species that carries the genetic determinant and that can be crossed with *Valerianella locusta*, such as *Valerianella carinata*. Optionally the genetic determinant is equivalent to the said genetic determinant as found in NCIMB42007.

Optionally after crossing with a related species, techniques such as embryo rescue, backcrossing, or other techniques known to the skilled person can be performed to obtain seeds of the interspecific cross, which seeds can be used as the source for further development of a non-transgenic *V. locusta* plant that shows the trait of a fruit width smaller than 1.7 mm, and/or a length/width ratio of the fruit higher than 1.2, and/or an improved germination of a batch of fruits of a certain fraction size as compared to a batch of *V. locusta* fruits of a certain fraction size not having the genetic determinant.

The invention also relates to the germplasm of plants of the invention. The germplasm is constituted by all inherited characteristics of an organism and according to the invention encompasses at least the trait of the invention. The germplasm can be used in a breeding programme for the development of *V. locusta* plants having the trait of a fruit width smaller than 1.7 mm, and/or a length/width ratio of the fruit higher than 1.2, and/or an improved germination of a batch of fruits of a certain fraction size as compared to a batch of *V. locusta* fruits of a certain fraction size not having the genetic determinant.

The invention further relates to a food product, which may comprise the corn salad plant or the leaves of a *V. locusta* plant as claimed, or parts thereof. The invention also relates to a food product in processed form.

In one aspect the invention relates to a method for production of a *V. locusta* plant which may comprise the trait of a fruit width smaller than 1.7 mm, and/or a length/width ratio of the fruit higher than 1.2, and/or an improved germination of a batch of fruits of a certain fraction size as compared to a batch of *V. locusta* fruits of a certain fraction size not having the genetic determinant, which may comprise:

a) crossing a plant which may comprise the genetic determinant that results in the trait of a fruit width smaller than 1.7 mm, and/or a length/width ratio of the fruit higher than 1.2, and/or and improved germination of a batch of fruits of a certain fraction size as compared to a batch of *V. locusta* fruits of a certain fraction size not having the genetic determinant, representative seed of which was deposited as NCIMB 42007, with a plant not comprising the genetic determinant to obtain an F1 population;

b) optionally performing one or more rounds of selfing and or crossing a plant from the F1 to obtain a further generation population;

c) selecting a plant that may comprise the genetic determinant that leads to the trait of a fruit width smaller than 1.7 mm, and/or a length/width ratio of the fruit higher than 1.2, and/or an improved germination of a batch of fruits of a certain fraction size as compared to a batch of *V. locusta* fruits of a certain fraction size not having the genetic determinant, suitably by using molecular markers linked to the genetic determinant.

The invention additionally provides a method of introducing a desired trait into a *V. locusta* plant which may comprise the trait of a fruit width smaller than 1.7 mm, and/or a length/width ratio higher than 1.2, and/or an improved germination of a batch of fruits of a certain fraction size as compared to a batch of *V. locusta* fruits of a certain fraction size not having the genetic determinant, which may comprise:

a) crossing a *V. locusta* plant which may comprise the trait of a fruit width smaller than 1.7 mm, and/or a length/width ratio higher than 1.2, and/or an improved germination of a batch of fruits of a certain fraction size as compared to a batch of *V. locusta* fruits of a certain fraction size not having the genetic determinant, representative seed of which were deposited with the NCIMB under deposit number NCIMB 42007, with a second *V. locusta* plant that may comprise a desired trait to produce F1 progeny;

b) selecting an F1 progeny;

c) crossing the selected F1 progeny with either parent, to produce backcross progeny;

d) selecting backcross progeny, optionally after one or more selfing steps, which may comprise the desired trait and the trait of a fruit width smaller than 1.7 mm, and/or a length/width ratio of the fruit higher than 1.2, and/or an improved germination; and e) optionally repeating steps c) and d) one or more times in succession to produce selected fourth or higher backcross progeny that may comprise the desired trait and the genetic determinant that leads to the trait of a fruit width smaller than 1.7 mm, and/or a length/width ratio of the fruit higher than 1.2, and/or an improved germination. The invention includes a *V. locusta* plant produced by this method and the *V. locusta* fruit obtained therefrom.

Selection for a plant which may comprise the genetic determinant of the invention can alternatively be done following any crossing or selfing step of the method. Selection can be done phenotypically, or suitably by using a molecular marker for the genetic determinant of the invention.

In one embodiment the plant which may comprise the genetic determinant either homozygously or heterozygously is a plant of an inbred line, a hybrid, a doubled haploid, or of a segregating population.

The invention further provides a method for the production of a *V. locusta* plant which may comprise the trait of a fruit width smaller than 1.7 mm, and/or a length/width ratio of the fruit higher than 1.2, and/or an improved germination by using a doubled haploid generation technique to generate a doubted haploid line that homozygously may comprise the said genetic determinant that leads to the trait of a fruit width smaller than 1.7 mm, and/or a length/width ratio of the fruit higher than 1.2, and/or an improved germination. The doubled haploid line is a plant of the invention, but can also be crossed with a line that lacks the said genetic determinant to generate a plant of the invention that may comprise the genetic determinant heterozygously.

The invention furthermore relates to hybrid seed and to a method for producing hybrid seed which may comprise crossing a first parent plant with a second parent plant and harvesting the resultant hybrid seed. Said first parent plant or said first parent plant and said second parent plant is a plant that may comprise the genetic determinant that results in a plant of the invention homozygously, and the resulting hybrid fruit is a fruit of the invention.

The invention also relates to a method for the production of a *V. locusta* plant which may comprise the genetic determinant that leads to the trait of a fruit width smaller than it 1.7 mm, and/or a length/width ratio of the fruit higher than 1.2, and/or an improved germination, by using a seed that may comprise a genetic determinant in its genome that leads to the trait of a fruit width smaller than 1.7 mm, and/or a length/width ratio of the fruit higher than 1.2, and/or an improved germination, for growing the said *V. locusta* plant. The seeds are suitably seeds of which a representative sample was deposited with the NCIMB under deposit number NCIMB 42007.

The invention also relates to a method for seed production which may comprise growing *V. locusta* plants which may comprise the genetic determinant, allowing the plants to produce seeds, and harvesting those seeds. Production of the seeds is suitably done by crossing or selfing.

In one embodiment, the invention relates to a method for the production of a *V. locusta* plant which may comprise the genetic determinant that leads to the trait of a fruit width smaller than 1.7 mm, and/or a length/width ratio of the fruit higher than 1.2, and/or an improved germination, by using tissue culture. The invention furthermore relates to a method for the production of a *V. locusta* plant which may comprise the genetic determinant that leads to the trait of a fruit width smaller than 1.7 mm, and/or a length/width ratio of the fruit higher than 1.2, and/or an improved germination, by using vegetative reproduction.

In one embodiment, the invention relates to a method for the production of a *V. locusta* plant which may comprise the genetic determinant that leads to the trait of a fruit width smaller than 1.7 mm, and/or a length/width ratio of the fruit higher than 1.2, and/or an improved germination, by using a method for genetic modification to introduce the genetic determinant of the invention that leads to a fruit width smaller than 1.7 mm, and/or a length/width ratio of the fruit higher than 1.2, and/or an improved germination into the *V. locusta* plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of *V. locusta* plants that comprise a genetic determinant that leads to a fruit width smaller than 1.7 mm, and/or a length/width ratio of the fruit higher than 1.2, and/or an improved germination, wherein germplasm which may comprise a genetic determinant that leads to a fruit width smaller than 1.7 mm, and/or a length/width ratio of the fruit higher than 1.2, and/or an improved germination is used. Representative seed of said plant which may comprise a genetic determinant in homozygous state was deposited with the NCIMB under deposit number NCIMB 42007.

In a further embodiment the invention relates to a method for the production of a *V locusta* plant which may comprise a genetic determinant that leads to a fruit width smaller than 1.7 mm, and/or a length/width ratio of the fruit higher than 1.2, and/or an improved germination, wherein progeny or propagation material of a plant which may comprise a genetic determinant that leads to the trait of the invention conferring a fruit width smaller than 1.7 mm, and/or a length/width ratio of the fruit higher than 1.2, and/or an improved germination, is used as a source to introgress a fruit width smaller than 1.7 mm, and/or a length/width ratio of the fruit higher than 1.2, and/or an improved germination into another *V. locusta* plant. Representative seed of said plant which may comprise the genetic determinant in homozygous state was deposited with the NCIMB under deposit number NCIMB 42007.

The invention provides preferably a *V. locusta* plant showing a fruit width smaller than 1.7 mm, and/or a length/width ratio of the fruit higher than 1.2, and/or an improved germination of a batch of fruits of a certain fraction size as compared to a batch of *V. locusta* fruits of a certain fraction size not having the genetic determinant, which plant is obtainable by any of the methods herein described.

The invention also relates to a method for the production of *V. locusta* fruits, which may comprise growing *V. locusta* plants which may comprise the genetic determinant that leads to the trait of a fruit width smaller than 1.7 mm, and/or a length/width ratio of the fruit higher than 1.2, and/or an improved germination, as described herein and allowing them to produce *V. locusta* fruits and optionally harvesting the fruits.

A genetic determinant can be identified by the use of a molecular marker. A genetic determinant can alternatively be identified by the position on a genetic map, or by indication of the location on a linkage group or chromosome. When a genetic determinant is not linked to a specific molecular marker any longer, but its position on a chromosome as defined on a genetic map is unaltered, this genetic determinant is still the same as when it was linked to the molecular marker. The genetic trait that it confers is therefore also still the same.

The 'genetic trait' is the trait or characteristic that is conferred by the genetic determinant. The genetic trait can be identified phenotypically. However, also plant stages for which no phenotypic assay can be performed do carry the genetic information that leads to the genetic trait. 'Trait' or 'phenotypic trait' can be used instead of 'genetic trait'. Furthermore, in case of a recessive trait heterozygous plants also carry genetic information that when present in homozygous form causes a fruit width smaller than 1.7 mm, and/or a length/width ratio of the fruit higher than 1.2, and/or an improved germination. Such plants are a source of the alleles and as such are also part of this invention.

In the present case, the trait is phenotypically seen as a fruit width smaller than 1.7 mm, and a length/width ratio of the fruit higher than 1.2. However, the improved germination of a batch of fruits of a certain fraction size is also part of the trait of the invention. The fruit width smaller than 1.7 mm, and the length/width ratio of the fruit higher than 1.2, act as a phenotypic marker for improved germination. Fruit width and length/width ratio should always be measured and compared on mature *Valerianella* fruits. Improved germination should always be compared on untreated batches of fruits.

When for a *Valerianella locusta* corn salad plant a reference herein is made to a *Valerianella carinata* fruit shape or *V. carinata* fruit type, this may comprise a fruit shape or fruit type that has a fruit width smaller than 1.7 mm, and/or a length/width ratio of the fruit that is higher than 1.2.

In the absence of molecular markers, or in the instance that recombination between the genetic determinant and the marker has taken place so that the marker is not predictive anymore, equivalence of genetic determinants can be determined by an allelism test. To perform an allelism test, a tester plant which is homozygous for the known determinant of the invention, and therefore shows the trait of the invention, is crossed with material to be tested that is also homozygous for its genetic determinant. When no segregation for the trait of the invention is present in the F3 seeds that are produced on the F2 plants of the test cross, the genetic determinants have been proven to be equivalent or the same. The trait of the invention in this instance is suitably observed as a fruit width smaller than 1.7 mm and/or a length/width ratio of the fruit higher than 1.2.

Equivalence of genetic determinants can also be determined in this manner. A genetic determinant is considered to be equivalent to the genetic determinant of the invention, as found in deposit NCIMB 42007, if minor sequence differences or mutations exist when compared to the genetic determinant of the invention, but the genetic determinant has the same chromosomal location, and is therefore an allele that still leads to the same trait of a fruit width smaller than 1.7 mm and/or a length/width ratio of the fruit higher than 1.2.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Development of a Fruit of the Invention

A *V. locusta* plant of the variety Cirilla (internal number 95138-M94174 86113 50-67) was used as a maternal parent and crossed with a *V. carinata* plant (internal accession number 93.500), which was used as the paternal parent. As a seed coat consists only of maternal tissue, the shape of the seed is expressed as a maternal effect, which means that the genotype of the maternal parent determines the shape of the seeds. Therefore the seeds and/or fruits sown as the F1 generation of the above mentioned cross all had a *V. locusta* shape, since the mother was a *V. locusta* parent. Seeds and fruits produced on the F1 plants also had the shape of *V. locusta*. As the genetic background for seed shape produced on the F1 plants must have been heterozygous, coming from both parents, it follows that the seed shape in this interspecific cross is inherited recessively. The sizes of the fruits in the F1 were variable.

The F2 generation is an inbred or self of the F1 generation and the F2 fruits sown were the ones produced on plants of the F1 cross, which F2 fruits all had a shape similar to *V. locusta*. The fruits produced on the F2 plants, i.e. the F3 fruits encompassing the F3 seeds, segregated in shape.

The F3 generation is again an inbred of the F2 generation. The fruits of the F3 generation were selected for the *V. carinata* phenotype for fruit shape. The selection was repeated in the F4 up to the F6 generation, whereby in each generation selection was done for the morphological characteristics of *V. locusta* plants, apart from the fruit type trait, for which selection for *V. carinata* type was done. Once a *V. carinata* was selected, no segregation was observed in the next generation. This confirmed the recessive inheritance of fruit shape in corn salad.

Finally in the F7 a plant was selected that morphologically and phenotypically had all the characteristics of cultivated *V. locusta*, but had the desired fruit type of *V. carinata*, for which it did not segregate any longer. The F7 generation was grown to form a bulk-population from approximately 100 selected plants from which batch 09.10211 was produced that was used for the deposit.

Example 2

Uniformity of Embryo's of Fruits of the Invention

Fruits of the invention were fractionalized, and the most common fraction of 1.5-1.75 mm was used to determine the size of the embryo. A batch of the same fraction was taken from *V. locusta* 'Cirilla', and the embryo's were measured as well. From the invention 60 embryo's were measured.

In addition, the embryo's of 60 and 50 fruits of fraction sizes of 2.0-2.25 mm and 2.25-2.5 mm of *V. locusta* 'Cirilla' were measured, since these sizes are the ones that are used very often commercially.

From fruits of the invention, the largest embryo that was measured was 2.3 mm, and the smallest one measured 1.8 mm. The average of 60 embryo's was 2.03 mm. The same fraction of 'Cirilla' had a minimum and maximum of 1.3 and 2.0 mm respectively, while the average size was 1.57 mm. The fraction sizes of 2.0-2.25 and 2.25-2.5 of 'Cirilla' both had a minimum embryo size of 1.4 mm, and a maximum of 2.1 and 2.2 mm respectively. The averages were 1.71 and 1.75 mm respectively (Table 3).

Next to *V. locusta*, also embryo sizes of fruits of *V. carinata* were measured. The fruits of *V. carinata* are of the same type as fruits of the invention. The embryo's of *V. carinata* measured 1.97 mm on average, with a range of between 1.7 and 2.2 mm.

In addition to the surprising result that embryo's of fruits of the invention were clearly larger than embryo's of fruits of the same fraction, and even of larger fractions, of *V. locusta* not carrying the genetic determinant of the invention, also the distribution in sizes was remarkably smaller. The standard deviation (SD) of embryo size of fruits of the invention was 0.14, while the SD of embryo size of *V. locusta* fruits that do not carry the genetic determinant of the invention was 0.18 for the same fraction, and 0.20 and 0.22 for the larger fractions (Table 3).

This means that fruits of the invention have an unexpectedly higher uniformity in seed and/or embryo size within a certain fraction size than fruits of *V. locusta* not carrying the genetic determinant of the invention.

Since a seed of *V. locusta* is primarily filled with the embryo, embryo size and seed size are highly correlated. The embryo size is measured as the length of the embryo.

Example 3

Germination of Corn Salad Fruits of the Invention 200 fruits of *V. locusta* 'Cirilla', *V. carinata* and *V. locusta* 09.10211 were sown on Mar. 16, 2012. All of the used batches had the same fraction size of 1.5-1.75 mm.

Already after four days it was clear that the fruits of the invention showed a very good germination. 64% of the fruits of 09.10211 had germinated after 4 days, while only 45% of the commercial 'Cirilla' and just 24% of *V. carinata*, having the same seed shape, had germinated (Table 4a).

After 5 days the fruits of the invention had germinated for 94%. This is already higher than the germination guarantee that is usually given when corn salad is sold commercially. A guarantee of 80% or 85% is common tier commercial batches. The fruits of the invention therefore show a remarkably good germination.

Fruits of the batch of the deposit even germinated for 100% after 7 days. The other batches reached only a germination of 83 and 93% in that same period. The genetic determinant of the invention has clearly resulted in an improved germination. The germination was better for speed, for uniformity, and for germination energy.

The improved germination was all the more surprising considering the fact that the related species *V. carinata* had not only the same fruit type but also the same embryo size as the fruits of the invention. This emphasizes that it is not just the type of the fruits as such, which may comprise a width smaller than 1.7 mm and/or a length/width ratio higher than 1.2, or the increased embryo size and/or seed size, that leads to improved germination. The improved germination is only observed when the genetic determinant from *V. carinata* leading to a fruit width smaller than 1.7 mm and/or to a length/width ratio of the fruit higher than 1.2 is introgressed into a *V. locusta* background.

Improvement of the germination through the introgression of the new fruit type which may comprise the enlarged embryo into *V. locusta* could therefore not have been predicted. The combination of a *V. locusta* genetic background with the new fruit type, having a width smaller than 1.7 mm and/or a length/width ratio higher than 1.2, has unexpectedly resulted in the present invention of an enlarged embryo and/or an improved germination.

The germination trial was repeated, and one more fraction of the variety Cirilla was added, as well as two batches of commercially available corn salad from the varieties Pulsar and Gala (Table 4b). Again, the corn salad of the invention outperformed all other materials included in the trial. Germination period was shorter and germination uniformity was better, as all seeds of the batch of the invention germinated within a period of 4 days. Germination was also faster, as the fruits of the invention had all germinated at 7 DAS. At 5 DAS already 84.5% of the seeds had germinated, which is very high.

Example 4

Plant Vigor of Corn Salad Plants of the Invention

Twenty plants grown from fruits of the invention were compared for biomass at harvest stage. The fraction used was again 1.5-1.75 mm, and comparison was done with 'Cirilla' and *V. carinata* plants grown from fruits of the same fraction size.

The average biomass of the rosette corn salad plant at stage of harvest was 2.6 g for *V. locusta* plants of 'Cirilla' that did not carry the genetic determinant of the invention. The size of plants grown from fruits of the invention at that same stage was much larger, as those plants had a biomass of 4.2 g. Plants grown from *V. carinata* weighed 3.8 g.

The new fruit type of the invention leads therefore to a major increase in yield per plant, as the plant vigor has been remarkably improved, leading to a higher biomass at harvesting stage.

Example 5

Transfer or the Trait of the Invention

A plant grown from a fruit of the invention was crossed with a *V. locusta* plant grown from a regular fruit without the genetic determinant of the invention. The F1 fruits as well as the F2 fruits phenotypically looked like *V. locusta* fruits, which may comprise large air chambers and a large fruit width. After selling, the F2 plants produced segregating fruit types that were sown as F3 plants.

Once a fruit type of the invention, which may comprise a small fruit width and diminished air chambers, was selected in the F3, the fruit type did not segregate anymore. The fruit type can therefore be seen as a recessive trait conferred by a single gene or by closely linked genes, which closely linked genes inherit as one. Through regular selection and selling a stable line containing the fruit type of the invention and preferred other characteristics for cultivated corn salad could be developed.

Fruits from F4 plants, having the genetic determinant of the invention homozygously, and showing the fruit type of the invention that has a width smaller than 1.7 mm and a length/width ratio larger than 1.2, were sown and compared with the *V. locusta* parent that did not have the fruit type of the invention. Comparison was done with 200 fruits in a germination trial that was sown at 15° C. with 100% relative humidity, and was kept in 24 hours dark conditions until no more extra germination was observed.

The germination trial confirmed that the fruit type of the invention improved germination, when compared to the control parent that did not have the genetic determinant of the invention. Uniformity of germination, speed of germination, and germination vigor were better than the control plants. All trait aspects that are the result of the presence of the genetic determinant, for fruit type and for germination, could therefore be transferred to other *V. locusta* plants.

An alternative approach was to backcross the plants growing from the fruit type of the invention in the F3 with the *V. locusta* line that did not carry the genetic determinant of the invention. Every second generation, when the trait of the invention became visible, backcrossing was done to obtain a line isogenic to the original *V. locusta* line, apart from the trait conferred by the genetic determinant of the invention.

The invention is further described by the following numbered paragraphs:

1. Corn salad fruit of the species *Valerianella locusta*, characterised by a fruit width which is smaller than 1.7 mm and/or a length/width ratio of the fruits which is higher than 1.2, and which fruit width and/or length/width ratio are/is determined by a genetic determinant which is as found in, or is obtainable from, fruits of which a representative sample was deposited under accession number NCIMB 42007, or is equivalent to the said genetic determinant in NCIMB 42007.

2. Corn salad fruit as in paragraph 1, wherein the fruit width in order of increased preference is smaller than 1.6 mm, 1.5 mm, 1.4 mm, 1.3 mm, 1.2 mm, 1.1 mm, 1.0 mm, 0.9 min.

3. Corn salad fruit as in paragraph 1 or 2, wherein the length/width ratio of the fruits is in order of increased preference higher than 1.3, 1.4, 1.5, 1.6, 1.7, 1.8, 1.9.

4. Corn salad fruit as in any one of the paragraphs 1-3, wherein a batch of fruits of a certain fraction size shows a more uniform distribution of embryo size as compared to a batch of fruits of a certain fraction size of *V. locusta* fruits not having the genetic determinant.

5. Corn salad fruit as in paragraph 4, wherein the standard deviation of the embryo size of a batch of fruits of a certain fraction size in order of increased preference is smaller than 0.18, 0.17, 0.16, 0.15, 0.14.

6. Corn salad fruit as in any of the paragraphs 1 to 5, wherein as a result of the presence of the genetic determinant in the *V. locusta* genome a batch of said fruits of a certain fraction size has an improved germination as compared to a batch of *V. locusta* fruits of a certain fraction size not having the genetic determinant.

7. Corn salad fruit as in paragraph 6, wherein the germination of a batch of fruits of a certain fraction size in order of increased preference is higher than 45%, 46%, 47%, 48%, 49%, 50%, 51% at 4 days after sowing, and/or higher than 81%, 82%, 83%, 84% at 5 days after sowing, and/or higher than 97% at 6 days after sowing, and/or higher than 98%, 99% at 7 days after sowing.

8. Corn salad fruit as in any of the paragraphs 6-7, wherein the germination of a batch of fruits of a certain fraction size in order of increased preference is at least 3% higher, 6% higher, 10% higher, 13% higher, 16% higher, 19% higher at 4 days after sowing as compared to a batch of parent fruits of *V. locusta* of a certain fraction size not having the genetic determinant, and/or at least 3% higher, 5% higher, 7% higher, 9% higher, 11% higher, 13% higher at 5 days after sowing as compared to a batch of parent fruits of *V. locusta* of a certain fraction size not having the genetic determinant, and/or at least 2% higher, 4% higher, 6% higher, 8% higher, 9% higher at 6 days after sowing as compared to a batch of parent fruits of *V. locusta* of a certain fraction size not having the genetic determinant, and/or at least 2% higher, 4% higher, 5% higher, 6% higher at 7 days after sowing as compared to a batch of parent fruits of *V. locusta* of a certain fraction size not having the genetic determinant.

9. Corn salad fruit as in any of the paragraphs 1-8, wherein a batch of said fruits of a certain fraction size further has a significantly larger embryo size as compared to the embryo size of a batch of *V. locusta* fruits of a certain fraction size not having the genetic determinant.

10. Corn salad plant of the species *V. locusta* that can be grown from a fruit as in any of the paragraphs 1-9, wherein the corn salad plant carries the genetic determinant.

11. Progeny of a *V. locusta* plant as in paragraph 10 or of a *V. locusta* fruit as in any of the paragraphs 1-9, comprising the genetic determinant.

12. Propagation material suitable for producing a plant as in paragraph 10 or 11, or a fruit as in any of the paragraphs 1-9, wherein the propagation material is suitable for sexual reproduction, and is in particular selected from microspores, pollen, ovaries, ovules, embryo sacs and egg cells, or is suitable for vegetative reproduction, and is in particular selected from cuttings, roots, stems, cells, protoplasts, or is suitable for tissue cultures of regenerabie cells, and is in particular selected from leaves, pollen, embryos, cotyledon, hypocotyls, meristematic cells, roots, root tips, anthers, flowers, seeds, fruits and stems, wherein a plant produced from the propagation material comprises the genetic determinant.

13. Food product, comprising the corn salad plant as in paragraph 10 or 11, or parts thereof, optionally in processed form.

14. Use of a plant as in paragraphs 10 or 11, or plants produced from the fruit of any of the paragraphs 1-9, or from the propagation materials as in paragraph 10 as germplasm in a breeding programme for the development of corn salad plants of the species *V. locusta* that have a fruit width that is smaller than 1.7 mm, and/or a length/width ratio that is higher than 1.2, and/or an improved germination.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A method of producing a corn salad fruit of the species *Valerianella locusta*, the fruit of which is characterised by a fruit width smaller than 1.7 mm and a length/width ratio of the fruits higher than 1.6, and wherein the fruit has diminished air chambers as compared to the sterile locules of *V. locusta*, the method comprising:

a) crossing, a plant of *Valerianella locusta* 09.10211, representative fruit deposited under accession number NCIMB 42007, or an F1 or selfed progeny thereof having retained a fruit width smaller than 1.7 mm and a length/width ratio of the fruits higher than 1.6 and wherein the fruit has diminished air chambers as compared to the sterile locules of *V. locusta*, or a *Valerianella carinata* plant, with a *Valerianella locusta* plant to obtain an F1 population;

b) crossing the F1 with itself or with another *Valerianella locusta* plant to obtain a further generation population; and c) selecting in a further generation population a plant the fruits of which are characterised by a fruit width smaller than 1.7 mm and a length/width ratio of the fruits higher than 1.6, and wherein the fruit has diminished air chambers as compared to the sterile locules of *V. locusta*.

2. The method as claimed in claim 1, wherein the fruit width is smaller than 1.6 mm, 1.5 mm, 1.4 mm, 1.3 mm, 1.2 mm, 1.1 mm, 1.0 mm, or 0.9 mm.

3. The method as claimed in claim 1, wherein the length/width ratio of the fruits is higher than 1.3, 1.4, 1.5, 1.6, 1.7, 1.8, or 1.9.

4. The method as claimed in claim 1, further comprising the step of d) performing one to ten additional rounds of selfing or crossing, and subsequently selecting for a *Valerianella locusta* plant, the fruits of which are characterised by a fruit width smaller than 1.7 mm and a length/width ratio of the fruits higher than 1.6, and wherein the fruit has diminished air chambers as compared to the sterile locules of *V. locusta*.

5. A method of producing a corn salad plant of the species *Valerianella locusta*, the fruit of which is characterised by a fruit width smaller than 1.7 mm and a length/width ratio of the fruit higher than 1.6, and wherein the fruit has diminished air chambers as compared to the sterile locules of *V. locusta*, the method comprising:
  a) crossing, a plant of *Valerianella locusta* 09.10211, representative fruit deposited under accession number NCIMB 42007, or an F1 or selfed progeny thereof having retained a fruit width smaller than 1.7 mm and a length/width ratio of the fruits higher than 1.6 and wherein the fruit has diminished air chambers as compared to the sterile locules of *V. locusta*, or a *Valerianella carinata* plant, with a *Valerianella locusta* plant to obtain an F1 population;
  b) backcrossing the F1 with one of the parents to obtain a further generation population; and
  c) selecting in a further generation population a plant the fruits of which are characterised by a fruit width smaller than 1.7 mm and a length/width ratio of the fruits higher than 1.6, and wherein the fruit has diminished air chambers as compared to the sterile locules of *V. locusta*.

6. The method as claimed in claim 5, further comprising the step of
  d) performing one to ten additional rounds of selfing or crossing, and subsequently selecting for a *Valerianella locusta* plant, the fruits of which are characterised by a fruit width smaller than 1.7 mm and a length/width ratio of the fruits higher than 1.6, and wherein the fruit has diminished air chambers as compared to the sterile locules of *V. locusta*.

7. The method as claimed in claim 5, wherein the fruit width is smaller than 1.6 mm, 1.5 mm, 1.4 mm, 1.3 mm, 1.2 mm, 1.1 mm, 1.0 mm, or 0.9 mm.

8. The method as claimed in claim 5, wherein the length/width ratio of the fruits is higher than 1.7, 1.8, or 1.9.

9. A plant of *Valerianella locusta* 09.10211, representative fruit deposited under accession number NCIMB 42007, or an F1 or selfed progeny thereof having retained a fruit width smaller than 1.7 mm and a length/width ratio of the fruits higher than 1.6 and wherein the fruit has diminished air chambers as compared to the sterile locules of *V. locusta*.

* * * * *